United States Patent [19]

Klein et al.

[11] 4,244,787
[45] Jan. 13, 1981

[54] APPARATUS AND METHOD FOR DETERMINING SERUM CONCENTRATES OF METABOLITES BY MONITORING DIALYSATE FLUID

[75] Inventors: Elias Klein, New Orleans, La.; Ronald L. Wathen, Louisville, Ky.

[73] Assignee: The United States of America as represented by the Secretary of the Department of Health, Education & Welfare, Washington, D.C.

[21] Appl. No.: 47,786

[22] Filed: Jun. 11, 1979

[51] Int. Cl.³ .................... G01N 27/30; G01N 27/46; G01N 3/14
[52] U.S. Cl. .................... 204/1 T; 204/195 B; 204/195 P
[58] Field of Search ............ 204/180 P, 1 T, 195 B, 204/195 M, 195 P; 195/103.5 C; 23/230 B; 424/12

[56] References Cited

U.S. PATENT DOCUMENTS

| | | | |
|---|---|---|---|
| 3,399,972 | 9/1968 | Skeggs et al. | 23/230 B |
| 3,654,113 | 4/1972 | Bochinski | 204/1 T X |
| 3,767,548 | 10/1973 | Okada et al. | 204/180 P |
| 3,776,819 | 12/1973 | Williams | 204/1 T |
| 3,838,033 | 9/1974 | Mindt et al. | 204/195 B |
| 3,869,354 | 3/1975 | Montalvo, Jr. | 204/1 T |
| 3,870,617 | 3/1975 | Bourat | 204/180 P X |
| 3,902,970 | 9/1975 | Levin | 195/103.5 C |
| 4,024,042 | 5/1977 | Enfors et al. | 204/195 P |

Primary Examiner—Arthur C. Prescott
Attorney, Agent, or Firm—Browdy and Neimark

[57] ABSTRACT

An apparatus and method are disclosed for monitoring, analyzing and quantitating in real time the concentrations of metabolites in serum by analyzing the dialysate solutions which are being equilibrated with the blood via a hemodialyzer. Thus, access to certain metabolically important species is provided without the necessity of blood sampling. The apparatus includes at least one ion-selective electrode coupled with the dialysate effluent stream, and the electrode EMF is converted to dialysate concentrations based on precalibration. The dialysate concentrations, in turn, are related to serum levels by factors governing mass transfer through the dialyzer.

12 Claims, 8 Drawing Figures

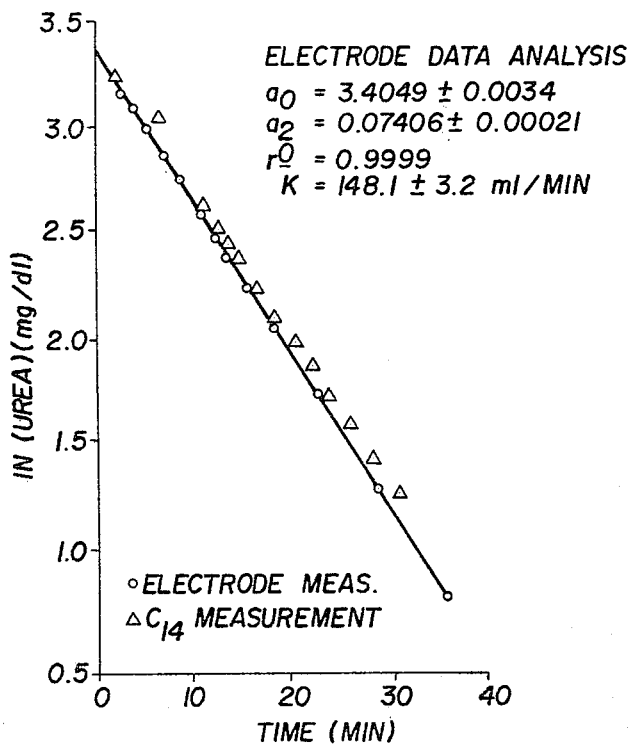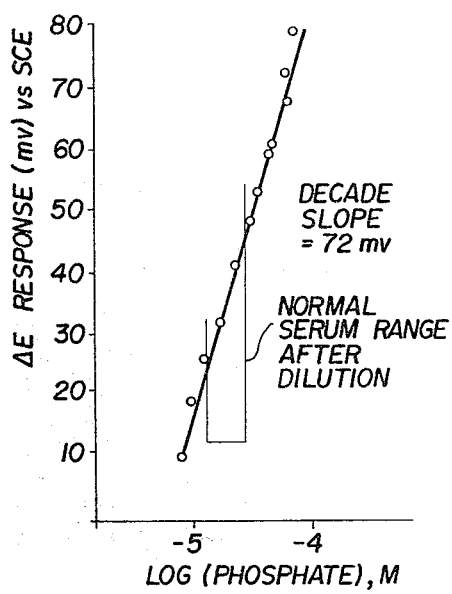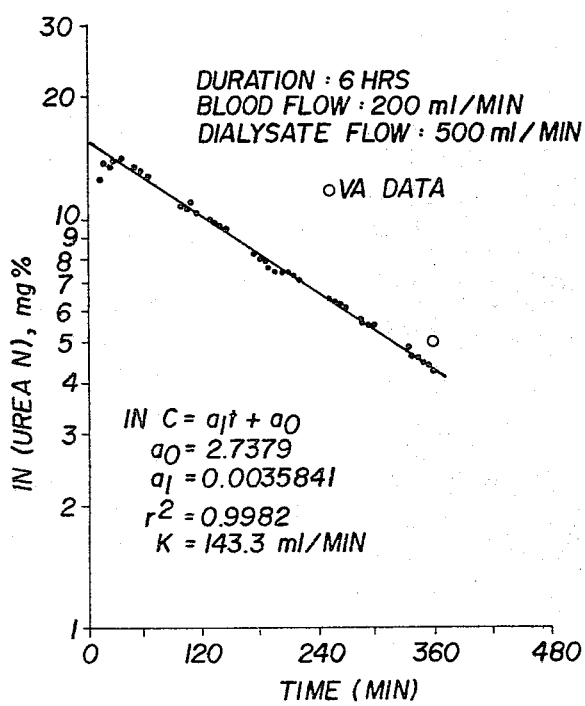

APPARATUS AND METHOD FOR DETERMINING SERUM CONCENTRATES OF METABOLITES BY MONITORING DIALYSATE FLUID

The invention described herein was made in the course of work under a grant or award from the Department of Health, Education and Welfare.

FIELD OF THE INVENTION

The present invention relates to an apparatus and method for the indirect monitoring of serum metabolites without entering a sensor into the patient's bloodstream or withdrawing blood from the patient. More particularly, the present invention relates to such a method and apparatus wherein the concentrations of metabolites in serum are monitored, analyzed and quantitated in real time by analyzing the dialysate solutions which are being equilibrated with the blood via a hemodialyzer.

BACKGROUND OF THE INVENTION

Significant use of dialysis therapy for patients suffering from renal disease has only been realized in recent years and the use of clinical chemistries to measure the progress of dialysis therapy is infrequent with end stage renal patients since the loss of blood for analysis must be held to a minimum in these patients because of chronically low hemocrits and because the cost of serum screens is high due to the operation of automated clinical analyzers for multiple factor analyses. As a consequence, the progress of most end stage renal patients on dialysis is followed only by a monthly assay for serum levels and by body mass measurement at each treatment session. However, it is generally recognized that a simple assay such as blood urea nitrogen (B.U.N.) would provide invaluable information on the progress of the therapy thereby enabling monitoring of the therapy and providing the opportunity for improved control of therapy. With prior art apparatus and methods such monitoring and control is accomplished by sampling the blood of the patient, and as noted previously, such techniques are not satisfactory.

SUMMARY OF THE INVENTION

An object of the invention is therefore to provide for improved blood monitoring; another object is to provide for improved dialysis; and a further object is to provide an improved apparatus and method for monitoring the progress of dialysis therapy.

Another object of the invention is to provide an apparatus by which the concentrations of metabolites in serum can be monitored, analyzed and quantitated by analyzing the dialysate solutions which are being equilibrated with the blood.

A further object of the invention is to provide an apparatus and method which provides biochemical data for monitoring of therapy and which utilizes the data for improved control of dialysis therapy.

A still further object of the invention is to provide an apparatus and method which utilizes dialysate fluid to monitor the progress of dialysis therapy.

An even further object of the invention is to provide an apparatus and method for providing one or several assays of serum metabolites during the course of dialysis therapy.

The present invention accomplishes the above objects by utilizing at least one ion-specific electrode which is contacted with a diverted portion of the dialysate effluent stream. The electrode EMF is converted to dialysate concentrations on the basis of pre-trial calibrations, and the dialysate concentrations, in turn, are related to serum levels by factors governing mass transfer through the dialyzer.

A knowledge of urea levels during dialysis can provide precise estimates to pre- and post-dialysis body levels of urea. From these, protein catabolism rates can be projected, from which metabolic acid and phosphate burdens and energy requirements for maintaining stable metabolism can be estimated. The present invention thus provides a simple means for automatic sensing and computation of metabolic balances and the procedures of the invention do not require blood access and are equally applicable to hemofiltration procedures or to hemo- and peritoneal dialysis.

In a specific example of the present invention, an aliquot of waste dialysate is sampled by a small peristaltic pump and metered with an equal volume of buffer solution into an immobilized urease column. During the passage of the solution through the column, the urea is hydrolized to ammonia and in the presence of the buffer the ratio of ammonium-ion to ammonia plus ammonium-ion is constant. This solution then passes through an ammonium-ion sensitive elctrode compartment and an EMF signal is provided via a pH meter to a strip-chart recorder or other data accumulating device. Prior to the beginning of dialysis, and at selected intervals during the treatment, calibrating solutions may be diverted from their respective reservoirs to the sensor. These calibrating solutions serve to detect any drifts in the electronics or other aberrations and in addition, they provide a check on the stability and response of the enzyme and electrode with time.

The above and other objects, advantages and the nature of the invention will be more readily apparent from the following detailed description of preferred embodiments taken in conjunction with the drawings, wherein:

BRIEF DESCRIPTION OF THE DRAWINGS

FIG. 3 is a graph showing the concentration of urea nitrogen in dialysate outflow plotted semi-logarithmically versus time.

FIG. 4 is a graph showing the potentiometric response curve of the phosphorous ion-selective electrode as a function of Monitrol II serum control concentration.

FIG. 5 is a graph of the computed, on-line dialysate urea nitrogen.

DETAILED DESCRIPTION OF THE PREFERRED EMBODIMENTS

Figure 1:
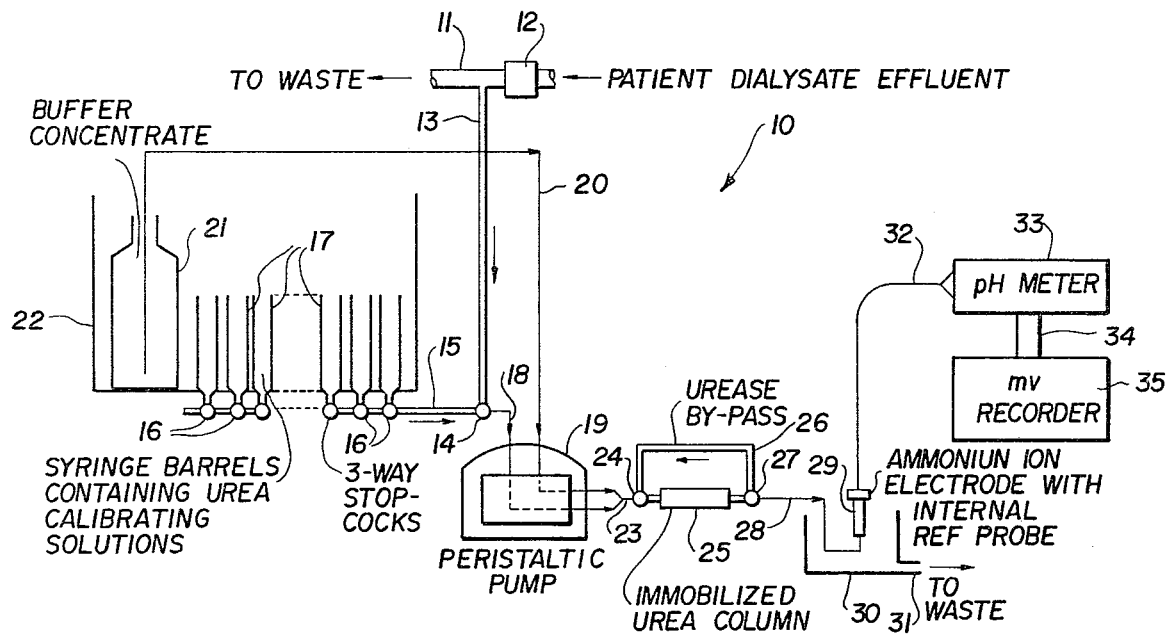
FIG. 1 is a somewhat diagrammatic view of an apparatus in accordance with the invention.

In the drawings, wherein like reference numerals indicate like parts throughout the several views, an apparatus for monitoring urea during dialysis therapy is indicated generally at 10 in FIG. 1. The apparatus includes a conduit 11 for conveying patient dialysate effluent to waste and a ball rotameter 12 is connected in the conduit 11 for measuring the dialysate flow rates. A branch conduit 13 is connected with the dialysate effluent conduit 11 for diverting a portion of the dialysate effluent to a three-way valve 14 connected in a calibration conduit 15 which is joined, in turn, with a plurality of three-way valves 16 provided at the base of a plurality of reservoirs 17 containing urea calibrating solutions. Downstream of the valve 14, the conduits 13 and 15 are combined into a single dialysate conduit 18 which leads to a peristaltic pump 19. A buffer conduit 20 extends from a container 21 of buffer concentrate to the peristaltic pump 19 for conveying buffer to the pump. The container 21 and reservoirs 17 may be supported in a suitable housing 22, if desired. Conduits 18 and 20 are combined downstream of the pump 19 into a single conduit 23 which leads to a three-way valve 24, connected in one position with an immobilized urease column 25 and in another position with a urease by-pass conduit 26, which extends between valve 24 and a second valve 27 downstream of the column 25. A discharge conduit 28 leads from the valve 27 downstream of the column 25 to an ammonium ion-sensitive electrode 29** with an internal reference probe. The electrode is extended into a receptacle or container 30 which has a waste or discharge connection 31 leading to a drain. Suitable wiring 32 leads from the electrode to a pH meter 33 which in turn is connected by coupling 34 with a suitable chart recorder or the like 35 for recording the output of the electrode 29 based upon the sensed concentration of the ammonium ion in the discharge from the column 25 through conduit 28.

\* Reference is made to Klein, "Progress in hemodialyzers and membranes-the last 20 years", Clinical Nephrology, Vol. 9 No. 4-1978 )pp. 131-137); and Klein et al, "Continuous monitoring of urea and inorganic phosphate during hemodialysis: II. Clinical trials", International Journal of Artifical Organs, Vol. 1 No. 4-1978 (pp. 175-180); copies attached and incorporated by reference.
\*\* see U.S. Pat. No. 3,869,354.

EXAMPLE I:

According to one example of the invention, an experiment was carried out at the New Orleans Veteran's Administration Hospital on a male patient with two ml/day of residual clearance, and who had been on dialysis for two years and was considered stable. The patient was monitored during the second and third treatment of a thrice weekly schedule. Blood access was through a bovine graft, and an Extracorporeal EX-04 hollow fiber—dialyzer (not shown) was used, and dialysate was provided by a Milton Roy central proportioning system (MED 1390) through a bedside station. Normal hemodialysis procedures were not altered except to route the waste dialysate solution to drain via a small container from which the analytical system sampled.

The analytical procedure was essentially as described in the International Journal of Artificial Organs, Volume 1, No. 3, pages 116 through 122 (1978), Klein, E., Montalvo, JG, Wawro, R., Holland, FF, and Lebeouf, A., except that the immobilized urease column 25 replaced the soluble enzyme preparation used previously. The apparatus illustrated in FIG. 1 was used for sensing the urea and an aliquot of the waste dialysate was sampled by the peristaltic pump and metered with an equal volume of buffer solution into the immobilized ureas column 25. During the passage of the solution through the column, the urea was hydrolized to ammonia (in the presence of the buffer the ratio of $NH_4^+/(NH_3+NH_4^+)$ is constant). The solution then passed through the ammonium ion-sensitive electrode compartment 30 and an EMF signal was conducted through line 32 to the pH meter 33, which in turn, supplied a signal to a strip-chart recorder 35 or other data accumulating device. Prior to the beginning of dialysis, and at selected intervals during the treatment, calibrating solutions were diverted from the reservoirs 17 to the conduit 15 and thence into conduit 18 and the electrode compartment. These calibrations serve to detect any drifts in the electronics or other aberrations. In addition, they provide a check on the stability and response of the enzyme and electrode with time. However, the results of the experiment indicated that such frequent calibration is not required and indications are that the urea electrode system can be operated with only a pre- and a post-dialysis calibration. The small drift observed during a six hour treatment period (2.5 mV) was linear in time and would thus not lead to serious errors.

Figure 2:
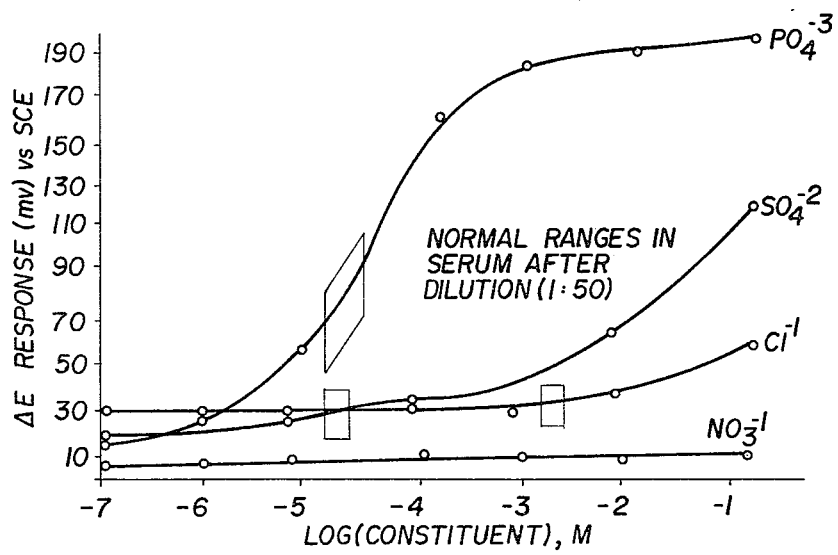
FIG. 2 is a graph of the potentiometric response curves of a phosphorous ion-selective electrode as a function of phosphate, sulfate, chloride and nitrate ion concentration.

A phosphate ($P_i$) electrode was operated in a similar manner except that no enzyme was used. Instead, a reservoir was used to maintain a constant partial pressure of oxygen since the response curve of this electrode is affected by the disolved $pO_2$ concentration. The sensitivity of the phosphate electrode is illustrated in FIG. 4, and its selectivity over other ions in FIG. 2. Because of the very dilute phosphate concentrations required to bring the levels to the linear response portion of the curve, the dialysate was diluted 50:1 with buffer. This dilution can also be performed with fresh dialysate containing additional buffer. However, it was more convenient to provide a separate diluent.

In order to provide a comparison of the results obtained by the indirect assay achieved with the apparatus of the invention, clinical procedures were followed utilizing blood samples taken at the beginning of dialysis, midway through dialysis treatment and at the termination of the dialysis treatment procedure. The blood samples were centrifuged after being allowed to settle for ten minutes and the plasma was analyzed by an Autoanalyzer. The accuracy of the procedures of the invention was found to be ±0.2 mg% for $P_i$ and ±0.2 mg% for serum urea nitrogen (SUN).

The dialysate flow rates were measured with the ball rotameter 12, calibrated prior to the experiment, and the blood flow was set by a calibrated blood pump (D-W No. 7404) (not shown) at 200 ml/min.

From the data obtained with the apparatus of FIG. 1, the arterial metabolite concentration ($C_B$) for a single pass dialysate system is related to the dialysate outflow concentration ($C_{Do}$) by $$C_B = C_{Do}(K/Q) \tag{1}$$

where Q is the dialysate flow rate in ml/min and K is the dialyzer clearance in ml/min. However, this relationship is valid only if the dialysate inlet solution is free of the metabolite. For assays of dialysate solution components which do have finite concentrations entering the dialyzer, such as $K^+$, $Na^+$ and acetate or bicarbonate ions, the procedure must be altered since the value of $C_{Di}$ is not zero. In these instances a difference analysis $(C_{Do} - C_{Di})$ is required. If there is a significant inlet concentration, as with $Ca^{2+}$, $K^+$, etc., the relationship becomes $$C_B = (C_{Do} - C_{Di})(K/Q) \tag{2}$$

where $C_{Di}$ and $C_{Do}$ are the inlet and outlet concentrations of the species in the dialysate fluid and $C_B$ is the arterial concentration. With the data obtained by analyzing the dialysate outlet fluid the serum arterial concentration can be determined via equations (1) and (2). Only the flow rate and the dialyzer clearance need be known. Moreover, the serum concentration itself is not the parameter needed for evaluation of the therapy. Rather, the total mass of such species transferred is desired and this can be achieved by summing the cross-product of the instantaneous concentration and the flow rate, i.e., $$M_i = \Sigma Q_D (C_{Do} - C_{Di})$$

For the computation of body $K^+$ burden, it is possible to measure the differential concentration $(C_{Do}-C_{Di})$ by use of differential electrodes. The product of this difference times the flow rate summed (or integrated, if a function is found) provides a measure of the mass of $K^+$ removed during dialysis. Since the $K^+$ burden is a important factor in the control of cardiac rate, and reflects intracellular protein neutralization, the control of this ion is important. In other words, in addition to providing needed biochemical data for the monitoring of therapy the procedure of the invention provides the opportunity for improved control of therapy. The analysis can be used as input data to a microprocessor which can then use the information to exercise control of the dialysis procedure. For example, if independent $K^+$ and urea assays are conducted and the target $K^+$ level is achieved before the urea level, the processor can initiate an infusion of $K^+$ to counteract the dialysis.

The assays described herein are based on well established mass transfer equations for the removal of metabolite by dialysis, i.e., $$K = Q_d \frac{(C_{DO} - C_{DE})}{C_{Bi}} = Q_B \frac{(C_{Bi} - C_{BO})}{C_{Bi}}$$

where $Q_d$ is the dialysate flow rate in ml/min., and K is the dialyzer clearance in ml/min.

Moreover, by either continuous or intermittent measurement of the dialysate outflow it is possible to determine not only the instantaneous serum levels but also the pre- and post-dialysis levels by extrapolation to zero time and to the end of dialysis.

For a metabolite which is distributed throughout the entire body water and whose intercompartmental transfer rates are high compared to the dialyzer clearance, the serum concentration during dialysis is given by $$Ln\ C_B = Ln\ C_B^o - (K/V)t \quad (3)$$

where $C_B^o$ is the pre-dialysis serum level, K is the dialyzer clearance and V is the body water volume. For urea, the assumptions necessary for this relationship have been established previously ($M = V_o C_o - V_t \cdot C_t$, where subscript o refers to pre-dialysis and subscript t refers to post-dialysis); however, for phosphate ions, the distribution and the intercompartmental transfer rates are not known and this relationship may be valid.

Figure 6:
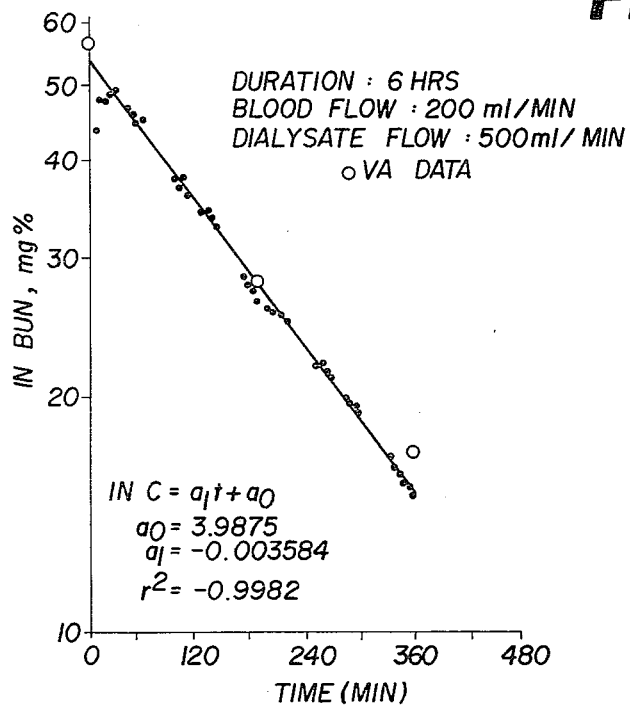
FIG. 6 is a graph of the computed, on-line blood urea nitrogen.

FIG. 5 shows the dialysate concentration versus time for urea during a six hour dialysis. The plot is linear on a semi-log scale as would be expected by substituting equation (1) into equation (3). The slope of the plot is given by K/V. Using a forty liter body water volume for the patient, the dialyzed clearance is calculated directly from the raw data. When these dialysate concentrations are converted to serum concentrations by equation (1) the results shown in FIG. 6 are obtained. The Autoanalyzer results reported by the clinical laboratory are also shown in this figure.

Five trials were carried out in a similar fashion. The pre-dialysis BUN calculated from regression plots of data illustrated by FIG. 6 are given in Table 1 together with the clinical measurements obtained by Autoanalyzer. The slope of log $C_{Do}$ versus time was also used to obtain the dialyzer clearance and these data are tabulated together with the correlation coefficient of the regression analysis.

TABLE I

REGRESSION ANALYSES OF $lnC_{sun}$ vs. t FROM DIALYSATE ANALYSES

| Experiment No. | $C^o$ (mg/dl) | K (ml/min) | $r^2$ | $C^o$(Blood)* | Ratio $C^o/C^o$(Blood) |
|---|---|---|---|---|---|
| 104 | 59.5 | 140 | .9965 | 60 | 0.99 |
| 105 | 61.5 | 151 | .9917 | 69 | 0.89 |
| 106 | 45.3 | 145 | .9963 | 52 | 0.87 |
| 107 | 53.9 | 143 | .9982 | 56 | 0.96 |
| 108 | 49.1 | 127 | .9948 | 55 | 0.89 |
| Mean | 53.9 | 141 | | 58.4 | 0.92 |
| St.Dev. | 6.8 | 8.9 | | 6.6 | 0.05 |

*By Autoanalyzer

Finally, it is possible to calculate the urea nitrogen removed from the patient by the relationship $$M = V_o C_o - V_t C_t$$

The patient on average lost 2.4 liters of isotonic water by ultrafiltration; the equation for this patient can thus be written to yield $$M = 400\ C_o - 376\ C_t$$

with concentrations in mg/dl nitrogen. These results are shown in Table 2.

TABLE II

| UREA NITROGEN MASS REMOVED DURING DIALYSIS | | | | |
|---|---|---|---|---|
| Trial No. | $C_o$ (mg/dl) | $C_t$ (mg/dl) | Mass Removed (gm) | $G_{BUN}$ (mg/min) |
| 104 | 59.46 | 16.85 | 17.45 | |
| 105 | 61.54 | 15.81 | 18.67 | |
| 106 | 45.25 | 12.20 | 13.51 | 4.4 |
| 107 | 53.92 | 14.84 | 15.99 | |
| 108 | 49.07 | 15.70 | 13.72 | 5.6 |

Figure 7:
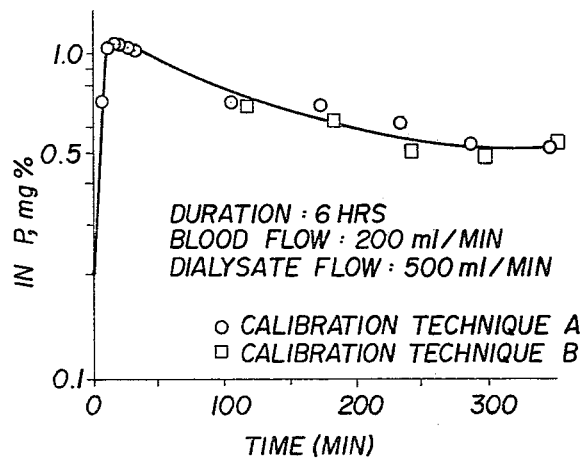
FIG. 7 is a graph of the computed, on-line blood phosphorus.
Figure 8:
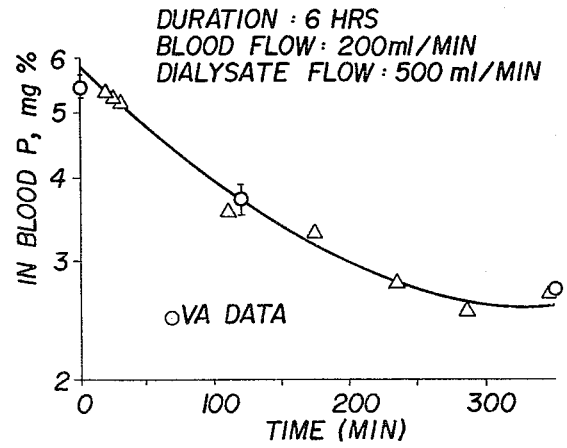
FIG. 8 is a graph of the dialysate outlet on-line phosphorus.

It is possible to compute urea generation rates using data from consecutive treatment periods. Using the relationships described by Gotch (Gotch, G. A., Sargent, J. A., Keen, M., Lamb, M., Prowitt, M. and Grady, M.: *Clinical Results of Intermittent Dialysis Therapy Guided By Ongoing Kenetic Analysis of Urea Metabolism*, Trans. Amer. Soc. Artif. Int. Organs, 22, 175 (1976)), it should also be possible to estimate the protein catabolism rates, phosphate burden and a metabolic acid generation for patients whose urea concentrations are known during each treatment. In the experiments conducted with the apparatus of the invention and set forth in Tables I and II, trials 105-106 and 107-108 were paired for the second and third dialyses of a thrice weekly schedule. Using the end values for trial 105 and the pre-dialysis value for trial 106, the generation rate (G) of serum urea nitrogen was calculated to be 4.4 mg/min. Similarly, for the 107-108 trial pair, the $G_{SUN}$ was found to be 5.6 mg/min. Two phosphate monitoring experiments were carried out. The first used intermittent aliquots of dialysate effluent from the patient's bedside calibration. The continuous monitoring trail is shown in FIG. 7, where the calculated blood inorganic phosphorous concentration is plotted as a function of tie together with the clinical lab results in plasma. Unlike the urea nitrogen results, this plot is not log-linear. The data indicates that transfer from a secondary pool of phosphate begins to dominate the serum concentrations during the latter half of the dialysis. These data are insufficient to determine whether this originates from tissue burdens or bone phosphate. The non-linearity of the Ln $P_i$ vs. time plot indicates that the serum values are not representative of total body levels over the time span of the dialysis. Therefore, it is not possible to use equation (3) to estimate total removal of inorganic phosphorus. However, integration of the area under the $C_{Do}$ vs. time curve provides an estimate of the $P_i$ removed, since the dialysate flow rate was constant. The data shown in FIG. 8 were used with manual integration and led to an estimate of 1200 mg $P_i$ removed during a six hour dialysis.

Thus, with the present invention, the blood levels of specific metabolites for various patients can be determined during the dialysis treatment without invasion of the circulation. The use of ion-selective electrodes coupled, when necessary, with enzyme provides a convenient method for continuous measurements. The data can be important in the control of therapy of end stage renal disease patients. The procedures are simple and are thus useful not only in a hospital situation, but also in limited care facilities or even with home patients. The invention thus makes the development of safer and more individually designed treatment protocols possible.

The foregoing description of the specific embodiments will so fully reveal the general nature of the invention that others can, by applying current knowledge, readily modify and/or adapt for various application such specific embodiments without departing from the generic concept, and, therefore, such adaptations and modifications should and are intended to be compehended within the meaning and range of equivalents of the disclosed embodiments. It is to be understood that the phraseology or terminology employed herein is for the purpose of description and not of limitation.

What is claimed is:

1. The method of determining the level of a predetermined metabolically important species in serum, without withdrawing blood or entering a sensor into the bloodstream, comprising the steps of:
   diverting at least a portion of a dialysate effluent stream, obtained from equilibration with blood through a hemodialyzer, through a sampling apparatus, including an ion-specific electrode sensitive to a desired species;
   producing an electrode EMF proportional to the concentration of the sensed species; and
   converting the EMF to data indicating the dialysate concentrations of the species and determining the serum levels of the species from such data.

2. The method as in claim 1, wherein:
   serum urea is monitored by diverting the dialysate effluent through an immobilized ureas column, wherein the urea is hydrolized to ammonia, and the concentration of ammonium-ion is sensed by the electrode.

3. The method as in claim 2, wherein:
   an equal volume of buffer solution is added to the dialysate effluent prior to sampling, thereof.

4. The method as in claim 1, wherein:
   serum phosphate is monitored by maintaining a partial pressure of oxygen in a reservoir of the dialysate effluent and a phosphate ion sensitive electrode is used to analyze the dialysate effluent.

5. The method as in claim 4, wherein:
   buffer is added to the dialysate effluent in the ratio of fifty parts buffer to one part dialysate effluent.

6. An apparatus for monitoring a blood serum metabolite by analyzing dialysate effluent equilibrated with blood via a hemodialyzer, comprising:
   diverting means for diverting at least a portion of the dialysate effluent into a sampling apparatus;
   sampling means in the sampling apparatus for selectively sampling a predetermined metabolite species present in the dialysate effluent, said sampling means including an ion-specific electrode for producing an EMF proportionate to the concentration of the species in the dialysate effluent; and
   means for converting the EMF to dialysate concentrations, which are, in turn, used to determine serum concentration of the species.

7. An apparatus as in claim 6, wherein:
   the sampling apparatus continuously samples the species in the dialysate effluent; and
   a recording device is connected to the means for converting the electrode EMF to record the species concentrations during hemodialysis.

8. An apparatus as in claim 6, further comprising:
   means to add a buffer solution to the dialysate effluent prior to sampling thereof, said means including a source of buffer solution; and means to pump an aliquot of said dialysate effluent and a selected quantity of buffer to said sampling means.

9. An apparatus as in claim 6, wherein:
   a plurality of calibrated solutions are connected to be added to the dialysate effluent prior to sampling thereof, to detect any drifts in the electronics, or other aberrations, and to provide a check on the stability and respone of the electrode with time.

10. An apparatus as in claim 6, wherein:
    the predetermined metabolite species is urea; the sampling apparatus includes an immobolized ureas column, through which the dialysate effluent is passed, during which the urea in the dialysate effluent is hydrolized to ammonia; and
    the electrode is a selective ammonium-ion sensitive electrode.

11. An apparatus for determining the level of a predetermined metabolically important species in serum, without withdrawing blood or entering a sensor into the bloodstream, comprising:
    diverting means for diverting at least a portion of a dialysate effluent stream, obtained from equilibration with blood through a hemodialyzer, through a sampling apparatus, including an ion-specific electrode sensitive to a desired species;
    means to produce an electrode EMF proportional to the concentration of the sensed species; and
    means to convert the EMF to data indicating the dialysate concentrations of the species and to determine the serum levels of the species from such data.

12. Apparatus as in claim 8, wherein said means to pump comprises a peristaltic pump, said means to add a buffer solution to the dialysate effluent comprising a line which joins with said diverting means downstream of said peristaltic pump;

said sampling means including an immobilized ureas column through which dialysate effluent is adapted to be passed for hydrolysis of urea to ammonia; and said ion-specific electrode is an ammonium-ion sensitive electrode with an internal reference probe.

* * * * *

UNITED STATES PATENT AND TRADEMARK OFFICE
CERTIFICATE OF CORRECTION

PATENT NO. : 4,244,787
DATED : January 13, 1981
INVENTOR(S) : KLEIN et al.

It is certified that error appears in the above-identified patent and that said Letters Patent are hereby corrected as shown below:

Column 3, line 65, "ureas" should read --urease--
Claim 2, line 3, "ureas" should read --urease--
Claim 10, line 3, "ureas" should read --urease--
Claim 12, line 6, "ureas" should read --urease--

Signed and Sealed this

Eighteenth Day of August 1981

[SEAL]

Attest:

Attesting Officer

GERALD J. MOSSINGHOFF

Commissioner of Patents and Trademarks